United States Patent
Clark et al.

(10) Patent No.: US 8,855,737 B2
(45) Date of Patent: *Oct. 7, 2014

(54) SYSTEM AND METHOD FOR ELECTRICALLY SHIELDING A MICROELECTRODE ARRAY IN A PHYSIOLOGICAL PATHWAY FROM ELECTRICAL NOISE

(71) Applicant: University of Utah Research Foundation, Salt Lake City, UT (US)

(72) Inventors: Gregory Arthur Clark, Salt Lake City, UT (US); David James Warren, Salt Lake City, UT (US); Noah M. Ledbetter, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/144,244

(22) Filed: Dec. 30, 2013

(65) Prior Publication Data

US 2014/0114164 A1    Apr. 24, 2014

Related U.S. Application Data

(63) Continuation of application No. 12/635,374, filed on Dec. 10, 2009, now Pat. No. 8,639,312.

(60) Provisional application No. 61/121,473, filed on Dec. 10, 2008.

(51) Int. Cl.
| A61B 5/0478 | (2006.01) |
| A61N 1/05 | (2006.01) |
| A61N 1/16 | (2006.01) |
| A61B 5/04 | (2006.01) |
| A61B 5/0484 | (2006.01) |

(52) U.S. Cl.
CPC .............. *A61B 5/04001* (2013.01); *A61N 1/16* (2013.01); *A61N 1/0551* (2013.01); *A61N 1/0556* (2013.01)
USPC ........... 600/378; 600/373; 600/393; 600/544; 607/117; 607/118

(58) Field of Classification Search
CPC ...................................................... A61B 5/685
USPC ......... 600/372, 373, 378, 383, 393, 544–545, 600/546; 607/116–118
See application file for complete search history.

*Primary Examiner* — Allen Porter, Jr.
(74) *Attorney, Agent, or Firm* — Thorpe North & Western LLP (57) ABSTRACT

A system and method for electrically shielding a physiological pathway from electrical noise is disclosed. The method includes the operation of implanting at least one signal microelectrode into a patient such that the signal microelectrode is proximate to the physiological pathway. An additional operation includes substantially enclosing the microelectrode and a section of the physiological pathway with an electrical shielding wrap. The electrical shielding wrap includes a plurality of holes that enable fluid communication of physiological fluids between an inside and outside of the wrap.

20 Claims, 4 Drawing Sheets

SYSTEM AND METHOD FOR ELECTRICALLY SHIELDING A MICROELECTRODE ARRAY IN A PHYSIOLOGICAL PATHWAY FROM ELECTRICAL NOISE

RELATED APPLICATIONS

This application is a continuation of U.S. patent application Ser. No. 12/635,374, now issued as U.S. Pat. No. 8,639,312, filed on Dec. 10, 2009, which claims the benefit of U.S. Provisional Patent Application No. 61/121,473 filed on Dec. 10, 2008, each of which is incorporated herein by reference. This application is also related to U.S. patent application Ser. No. 11/807,764, now issued as U.S. Pat. No. 7,951,300, filed May 29, 2007, entitled "WAFER SCALE NEEDLE ARRAY", U.S. patent application Ser. No. 11/807,763, filed May 29, 2007, entitled "MASKING HIGH ASPECT-RATIO STRUCTURES", U.S. patent application Ser. No. 11/807,766, filed May 29, 2007, entitled "MICRO-NEEDLE ARRAYS HAVING NON-PLANAR TIPS AND METHODS OF MANUFACTURE THEREOF", and U.S. Patent Application 61/041,819, filed Apr. 2, 2008, entitled "MICRO-ELECTRODE ARRAY SYSTEM WITH INTEGRATED REFERENCE MICROELECTRODES TO REDUCE DETECTED ELECTRICAL NOISE AND IMPROVE SELECTIVITY OF ACTIVATION", each of which are hereby incorporated by reference.

GOVERNMENT RIGHTS

This invention was made with government support under Award #N66001-05C-8045 awarded by the Unites States Department of Defense/Defense Advanced Research Projects Agency. The Government has certain rights in this invention.

BACKGROUND

1. Field of the Invention

The present invention relates generally to microelectrode array devices and methods of electrically shielding physiological pathways within a body.

2. Related Art

The potential for implanting electronic devices into patients with direct interface to the neural system is vast. Systems which may enable paraplegics to regain control of their bladder or limbs, provide vision for the blind, or restore vocal cord function are all under development, and promising initial results have been obtained in some experiments.

A key component of some implantable systems is a needle array to enable interfacing of the electronics with a nerve or directly with neuron in brain tissue. For example, U.S. Pat. No. 5,215,088 to Normann et al. discloses a three-dimensional electrode device which can be used as a neural or cortical implant. The devices of Normann, also known as the Utah Electrode Array (UEA) and the Utah Slanted Electrode Array (USEA), respectively, can be used to provide a neural interface to electronic equipment for sensing and/or stimulation of physiological signals and pathways and has been successfully used in a large number of patients. However, difficulties and challenges of this system are still present which limit its effectiveness and potential applications. Biological organisms, from the simple to the substantially complex, can include a wide range of different physiological signals and pathways for the signals to travel. The large number of different signals and pathways can cause biological organisms to be a relatively noisy electrical environment. Neural and nerve impulses tend to have a relatively low amplitude in comparison to surrounding competing signals from other physiological systems, e.g. muscles. Accurately sensing and/or activating these signals and pathways within this noisy environment can be challenging.

SUMMARY

A system and method for electrically shielding a physiological pathway from electrical noise is disclosed. The method includes the operation of implanting an array of signal microelectrodes on a dielectric substrate into a patient such that the signal microelectrodes are proximate to the physiological pathway. An additional operation includes substantially enclosing the array and a section of the physiological pathway with an electrical shielding wrap. The electrical shielding wrap includes a plurality of holes that enable fluid communication of physiological fluids between an inside and outside of the wrap and can optionally allow the transmission of certain desired electrical and magnetic signals to pass through the shield while blocking other undesired signals.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

It will be understood that these figures are provided merely for convenience in describing the invention and are drawn for purposes of clarity rather than scale. As such, actual dimensions may, and likely will, deviate from those illustrated in terms of relative dimensions, contours, and the like. For example, FIG. 2c illustrates an embodiment showing a microelectrode array with 13 electrodes along a side. The array may vary from a few electrodes to hundreds or even thousands along a side. Similarly, for purposes of clarity FIGS. 3a-3d are idealized and simplified versions of a nerve bundle and wrap.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

In describing embodiments of the present invention, the following terminology will be used.

The singular forms "a," "an," and "the" include plural referents unless the context clearly dictates otherwise. Thus, for example, reference to "a needle" includes reference to one or more of such needles and "etching" includes one or more of such steps.

As used herein, "substantial" when used in reference to a quantity or amount of a material, or a specific characteristic thereof, refers to an amount that is sufficient to provide an effect that the material or characteristic was intended to provide. Therefore, "substantially free" when used in reference to a quantity or amount of a material, or a specific characteristic thereof, refers to the absence of the material or characteristic, or to the presence of the material or characteristic in an amount that is insufficient to impart a measurable effect, normally imparted by such material or characteristic.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "50-250 micrometers should be interpreted to include not only the explicitly recited values of about 50 micrometers and 250 micrometers, but also include individual values and sub-ranges within the indicated range. Thus, included in this numerical range are individual values such as 60, 70, and 80 micrometers, and sub-ranges such as from 50-100 micrometers, from 100-200, and from 100-250 micrometers, etc. This same principle applies to ranges reciting only one numerical value and should apply regardless of the breadth of the range or the characteristics being described.

As used herein, the terms "about" or "approximately" mean that dimensions, sizes, formulations, parameters, shapes and other quantities and characteristics are not and need not be exact, but may be approximated and/or larger or smaller, as desired, reflecting tolerances, conversion factors, rounding off, measurement error and the like and other factors known to those of skill. Further, unless otherwise stated, the terms "about" and "approximately" shall expressly include "exactly," consistent with the discussion above regarding ranges and numerical data.

As used herein, the term "signal electrode(s)" may refer to an electrode or electrodes used for recording, stimulation, or both.

Electrically Shielded Containment Systems

As mentioned above, accurately sensing signals within the relatively noisy electrical environment of a biological organism can be challenging. However, accurate sensing of signals and and/or stimulation of physiological tissue to form signals can provide effective strategies for repairing or replacing nervous system components within a biological organism. For example, a fundamental challenge for effective motor and sensory neuroprotheses is selective activation—the ability to activate specific nerve fibers, while sparing or inhibiting others. To provide effective control, one should be able to communicate specific instructions to the nervous system without also issuing contradictory or interfering commands. Present-day electrical interfaces offer only limited capabilities for selective activation, thereby limiting the ability to restore natural motor or other sensory functions.

Additionally, accurate measurements of physiological signals within a body can be used to provide control of artificial and biological devices. For example, measurements of motor neural signals sent to or travelling down a nerve within a body can be used to control an artificial device such as an artificial appendage, or distal body parts. Similarly, sensory information travelling along sensory nerve fibers or elsewhere can be detected and then used to provide cutaneous, proprioceptive, or other types of sensory feedback and information to an individual. These neural signals can be relatively small, on the order of tens to hundreds of microvolts, requiring a low level of background noise in order for the signals to be accurately detected. Hence, in order for the signal to be accurately detected, interpreted, and communicated, it can be helpful to reduce or eliminate various types of electrical noise within a body, emanating from either outside the body (e.g., 60-Hz power-line noise) or from within the body (e.g., electrical signals from heart or muscle), when one desires to record electrical discharges of neurons or axons.

Figure 1A:
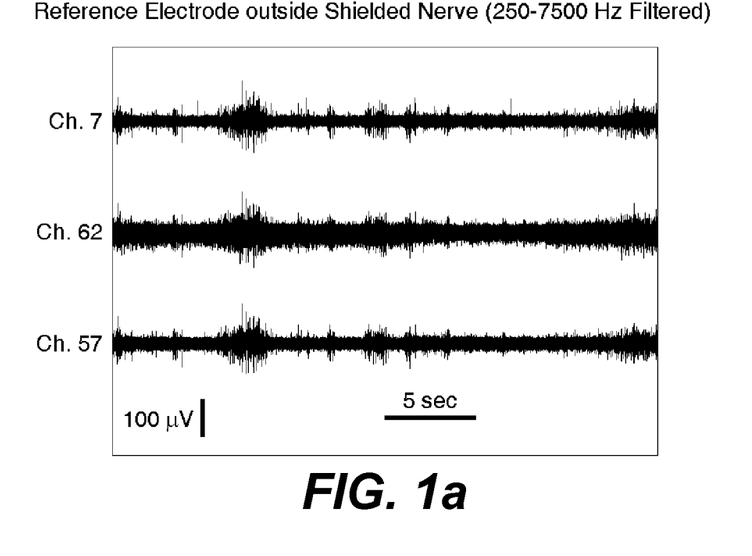
FIG. 1a is a graph showing electrical measurements of a nerve with a reference electrode implanted in surrounding muscle tissue in accordance with the prior art.

For example, FIG. 1a illustrates a measurement made using a variation of the Utah Electrode Array (UEA), referred to as the Utah Slanted Electrode Array (USEA). The USEA includes an array of microelectrodes integrated on a dielectric substrate. The microelectrodes are positioned substantially perpendicular to the substrate. The rows have a progressively decreasing height with respect to the dielectric substrate. The variation in the height of the electrodes can allow measurement of different types of neuronal action potentials, i.e. by virtue of increasing tip depth. The USEA was implanted into the sciatic nerve of a feline. According to the conventional approach, a discrete metal wire electrode was placed in the muscular tissue surrounding the sciatic nerve to act as a reference electrode. The USEA was then activated to receive neural recordings of active signals within the sciatic nerve.

However, electromyogram (EMG) signals from the surrounding muscle tissue provide significant noise on all three channels recorded within the sciatic nerve. It can be difficult to distinguish the neural signals from the background noise in the surrounding tissue.

Figure 1B:
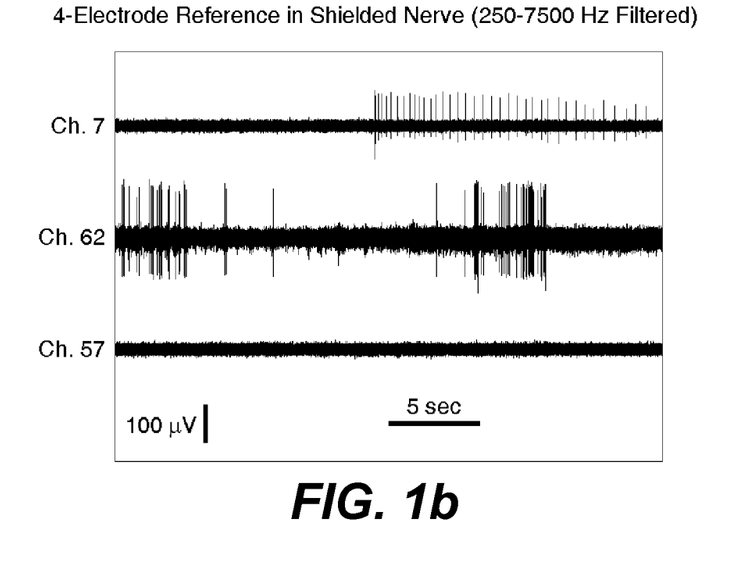
FIG. 1b is a graph showing electrical measurements of the nerve in FIG. 1a with reference electrodes integrated with signal electrodes in accordance with an embodiment of the present invention.

FIG. 1b illustrates the same measurement using a plurality of large tipped, low-impedance electrodes located in the array on the dielectric substrate as the reference, rather than the discrete wire. Additionally, a flexible, electrically grounded shield was also used as part of a containment system around the array. Channels 7 and 62 in FIG. 1b, representing two of the microelectrodes in the array, show neural activity that is recorded within the sciatic nerve. With the reduction in noise it can be seen that no neural activity is detected on channel 57. The neural activity recorded in FIG. 1b has a substantially reduced level of noise from EMG signals in the surrounding tissue. The reduced level of noise enables the neural signals to be easily distinguished from the noise.

Figure 2A:
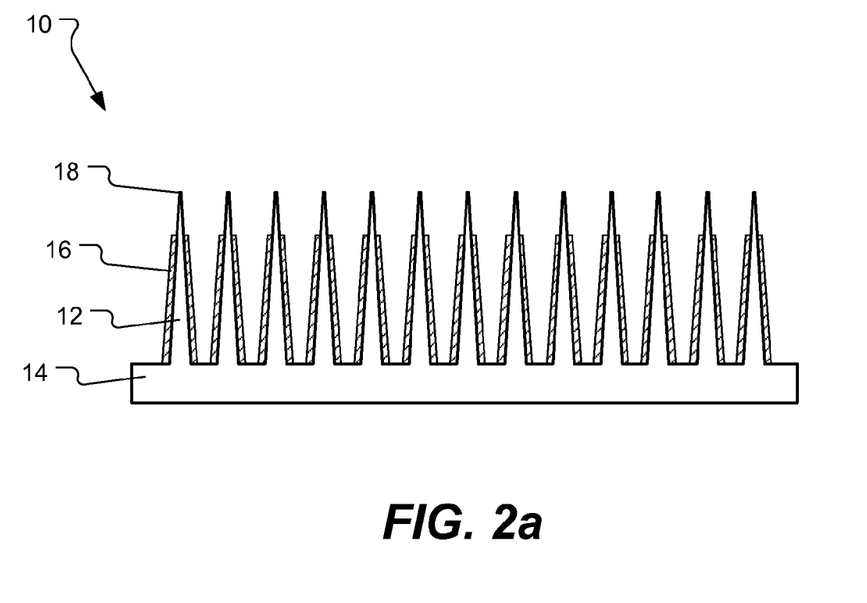
FIG. 2a is a side view of an illustration of a microelectrode array with electrodes having substantially equal height.

One exemplary embodiment of the microelectrode array is illustrated in FIG. 2a. The array can include an array of micro-electrodes 12 extending upward from the dielectric substrate 14. Typically, each of the micro-electrodes are individually addressable, i.e. separated from one another via a dielectric material such as epoxy or glass. The dielectric substrate can be a silicon wafer, enabling a plurality of arrays to be formed at one time using known lithographic and/or micromachining techniques. The array of electrodes may be formed from a single substrate, e.g. a three dimensional array. Alternatively, a plurality of microelectrodes formed on different substrates can be coupled together to form the array, e.g. a plurality of two dimensional arrays can be combined to form the three dimensional array. Alternatively, a two dimensional array having a single row of electrodes can also be used. In some cases, a single signal microelectrode may be used. A typical microelectrode array, such as the UEA, can include a 10×10 array of electrodes, although the array is not limited to a small number of electrodes. Nor is the array necessarily square. A different number of electrodes may be formed in each of the two dimensions, such as an array of 100×200 electrodes. The microelectrode array may include hundreds to thousands of micro-electrodes in each dimension of the array.

The electrodes can optionally include a coating 16. In one aspect, this coating can be an insulating material such as, but not limited to, parylene-C, silicon carbide, ceramics, or other insulating polymers. The coating can be removed from the tips 18 of the electrodes, enabling the tips to be electrically conductive. The coating can be removed using etching, laser ablation, or other suitable method that enables a predetermined portion of each electrode to be substantially free of the coating. The coating can reduce cross-talk between the electrodes and concentrate electric potential around a desired neuron or nerve. The coating can also reduce the level of background noise that is received by the microelectrodes.

The electrodes in a microelectrode array are typically manufactured to come to a point at the top. At the base, the electrodes may be circular, oval, square, rectangular, or have an irregular shape. In one embodiment, each electrode is independently electrically addressable. This enables a specific signal to be transmitted through a desired electrode. In another embodiment, the array can be addressed by column or row. In yet another embodiment, the entire array can be electrically connected such that a single signal can be sent through the array.

Figure 2B:
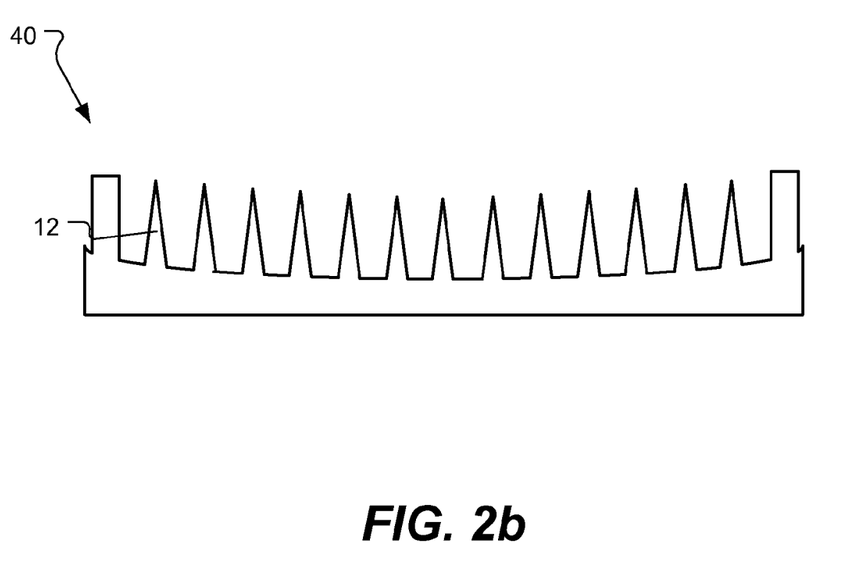
FIG. 2b is a side view of an illustration of a microelectrode array with electrodes having varying heights.
Figure 2C:
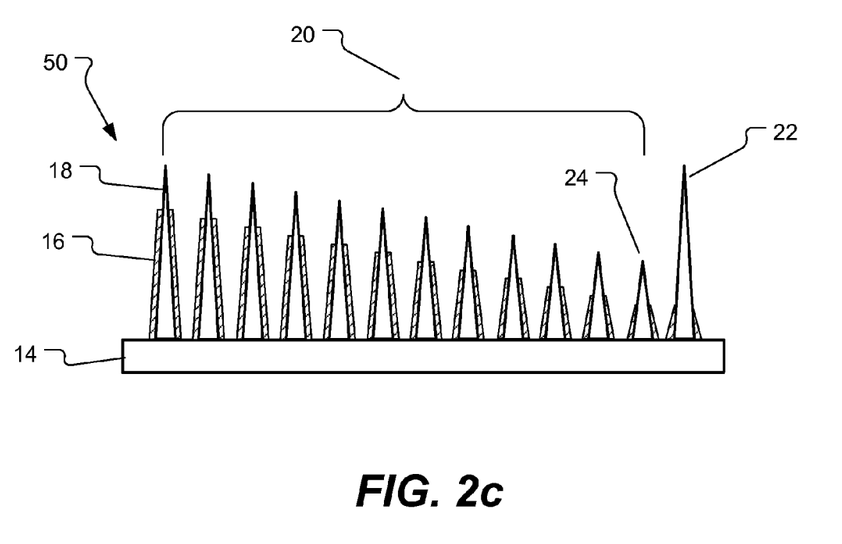
FIG. 2c is a side view of an illustration of a microelectrode array with rows of signal electrodes having progressively decreasing height and a reference electrode row adjacent a shortest row of the signal microelectrodes in accordance with an embodiment of the present invention.

In one embodiment, the microelectrode array 10 can be configured such that each of the microelectrodes 12 have a substantially uniform height relative to the substrate 14. In another embodiment, the micro-electrodes may vary in height. For example, FIG. 2b illustrates a microelectrode array 40 with the micro electrodes 12 configured to vary in height with a spherical concave shape. Similarly, FIG. 2c illustrates a microelectrode array 50 with each row having a progressively decreasing height with respect to the dielectric substrate 14. As previously discussed, this variation in height in the electrodes can increase the number of signals that can be sensed and the types of tissue that can be stimulated using the array when it is interfaced with tissue within a body, such as a muscle, a nerve, the brain, and so forth. FIG. 2c illustrates a plurality of rows of signal microelectrodes 20 and a row of reference microelectrodes 22 located adjacent the shortest row 24 of signal microelectrodes. As used herein, the term signal microelectrode is intended to include one or more microelectrodes that are configured to sense signals in a complex physiological solution. The term signal microelectrodes or signal electrodes can also be used to include one or more microelectrodes that are configured to stimulate tissue to form or initiate signals in the complex physiological solution. In one embodiment, a signal microelectrode may be able to both sense a signal and stimulate tissue to initiate a signal. In another embodiment, a signal microelectrode may be specifically configured to either sense signals or stimulate tissue.

The reference 22 and signal 24 microelectrodes can be formed from a single substrate 14. Alternatively, they can be formed on different substrates and coupled to form a single array. The reference and signal microelectrodes can be substantially perpendicular to the substrate. Constructing the microelectrodes to be perpendicular to the substrate provides mechanical strength to the electrodes, enabling the array to be implanted in various kinds of tissue with minimal damage to the electrodes during insertion and use.

In one embodiment, the reference microelectrodes 22 can be located in a single row, as illustrated in FIG. 2c. In another embodiment, multiple rows of reference microelectrodes may be formed on the substrate 14. Alternatively, the reference microelectrodes may be located at the corners of the array, around the perimeter of the array, at the center of the array, or alternating between signal microelectrodes 20 within the array. The actual positioning of the reference microelectrodes depends upon the use of the microelectrode array and the desired type of signal sensing or stimulus being performed. The reference microelectrodes may be positioned to minimize the level of radio frequency interference and background signals that are received at the signal microelectrodes. For example, placing the reference microelectrodes in a row or column or along a perimeter of the array can help to reduce the level of EMG signals, as illustrated in FIG. 1b.

Various methods have been developed to apply the coating 16 of insulating material over the microelectrodes while leaving the tips 18 of the electrodes substantially exposed to enable signals to be sensed and stimulated. For example, U.S. patent application Ser. No. 11/807,763, entitled "MASKING HIGH ASPECT-RATIO STRUCTURES" discloses a method for using lithographic processes to remove the insulating material from the tips. This process works especially well at exposing a plurality of tips over a relatively straight line. Thus, the process enables a tip of relatively equal height to be exposed over the array with progressively decreasing height, as shown in FIG. 2c.

However, unlike the signal electrodes, the inventors have found that the function of the reference electrodes is improved when a greater surface area of the reference electrodes is exposed. A greater amount of exposed area on the reference microelectrode enables the reference microelectrode to have a lower impedance, compared with the impedance of a typical recording electrode, for example, which may have an impedance of tens or even hundreds of Kohms (measured at 1 KHz). A minimized reference impedance approaching a value of zero ohms can enable the reference microelectrodes to provide the best signal to the signal electrodes.

Thus, it has been discovered that a substantial portion of the insulative coating 16 can be removed from the reference electrodes 22 by placing one or more rows of reference electrodes adjacent to the shortest row 24 of signal electrodes 20. The same process can be used to substantially bare the tips 18 of the signal electrodes to a desired height while also substantially removing the insulative coating from the reference electrodes, thereby maximizing the surface area of the reference electrodes while maintaining the tip size of the array of signal electrodes having decreasing height. This allows the microelectrode array with integrated reference electrodes to be manufactured without additional steps needed to produce a relatively large conductive surface area on the reference electrodes. In one embodiment, the row(s) of reference electrodes can be substantially the same height as the tallest row of signal electrodes. In another embodiment, the reference electrodes can have a greater height than any of the signal electrodes with respect to the substrate 14.

The exposed portion of the reference electrodes 22 may be coated with a conductive material such as a metal or alloy to provide greater conductivity. The signal microelectrode tips 18 may also be coated with a selected conductive or biological material to enable the tips to sense or stimulate a desired physiological signal.

The reference electrodes 22 on the microelectrode array 50 can be used to measure potential or to apply a current. When the signal electrodes 20 are used to sense a physiological signal within a body, the reference electrodes can be used as an electrical reference for the signal. Thus, the electrical potential or voltage can be measured between one or more signal microelectrodes and one or more reference microelectrodes.

The signal microelectrodes 20 can also be used to apply a current, with one or more signal microelectrodes acting as a cathode and one or more reference microelectrodes 22 or other electrodes acting as an anode, or vice versa. When the return electrodes or reference electrodes are located distant from the stimulating electrode, the result is referred to as monopolar stimulation. When the reference electrode is located relatively close, such as adjacent to the stimulating electrode, the result is referred to as bipolar stimulation. Various combinations of electrodes can be used to produce multipolar stimulation, allowing focusing and steering of currents. Monopolar, bipolar, and multipolar stimulation can be used to activate and deactivate various physiological pathways within the body. Different degrees and specificity of activation and deactivation can be achieved by varying number of electrodes used and which particular electrodes are used, as well as by varying stimulus strength, polarity, frequency, shape of pulses, and other stimulus parameters, in conjunction with physiological parameters such as fiber type and diameter, myelination, proximity of electrode to the fiber or node of Ranvier for that fiber, and the like.

The signal microelectrodes are typically independently addressable, enabling signals to be measured and applied at each signal microelectrode. However, it may be beneficial to electrically connect two or more of the signal microelectrodes. The reference microelectrodes may also be electrically isolated from adjoining reference microelectrodes. Alternatively, the reference microelectrodes may be connected together in series or parallel.

Connecting the reference microelectrodes together can create a common reference with a larger surface area. One or more rows of reference microelectrodes that are interconnected may also be used to provide additional radio frequency shielding to the signal microelectrodes. The row(s) of reference microelectrodes may further act as a partial faraday cage, shielding the signal microelectrodes from signals that radiate through the tissue in which they are implanted, thereby helping to isolate the signal electrodes from physiological signals generated in surrounding tissue. Additional shielding can also be placed around the microelectrode array when it is implanted, such as a flexible electrically grounded shield that can be used to help minimize noise detected from surrounding tissue or physiological processes. Creating larger surface area for the on-array reference electrodes, either by increasing tip size or number of reference electrodes, or both, can also reduce the possible contamination by a local neural signal near the reference electrode(s) which might then occur on all signal electrodes. The amplitude of the neural signal recorded by the reference(s) will be reduced by virtue of being averaged across a large area, most of which is not generating that signal.

The integration of reference electrodes into the array of microelectrodes or use of different selected electrodes on the array can enable bio-based selective stimulation that can mimic normal physiological activation patterns within a body. For example, specific fibers within a nerve can be activated while sparing or inhibiting activation in others. Selective activation can enable effective neuromotor control. Fibers within a given nerve can act as wire bundles within the body. Different fibers within a nerve bundle can go to different (and sometimes opposing) muscles. An implanted array of microelectrodes with integrated microelectrodes can provide selective activation of certain muscle groups, selective activation of fibers within a muscle, and selective inhibition of other muscle groups. This capability may provide excellent control of skeletal muscles used in voluntary movement, or other types of muscle including but not limited to smooth muscle, such as muscles involved in bladder control.

The microelectrode array can also be used to activate specific fiber types within a muscle according to the normal physiologic order, in order to produce finely graded, fatigue resistant responses. Additionally, unlike skeletal muscles, smooth muscles (such as the bladder) receive both excitation and inhibition signals. Hence, it is necessary to turn off one set of neural inputs selectively, while selectively turning on the other. Conventional nerve cuff electrodes and stimulation techniques are relatively ineffective at achieving selective activation.

Activation of specific types of fibers within a muscle can be important to reducing fatigue. For example, the calf (gastrocnemius) muscle is composed of both slow, small weak, fatigue-resistant (S) type fibers, and large, powerful, fast fatigable (FF) fibers. It is important to activate the S fibers first, as occurs in normal physiology, in order to achieve finely graded, fatigue resistant responses. But because large fibers are easier to activate with extracellular currents, conventional stimulation techniques typically produce the reverse, inappropriate recruitment order. Selective deactivation can be used to overcome this limitation.

Selective deactivation can also be used to block undesired, spontaneous activity in nerve fibers. Spontaneous activity (or evoked, pseudo-spontaneous activity) can be blocked by sending a neural signal from the microelectrode array to collide with and effectively cancel out the original, undesired nerve impulse.

As previously discussed, electrical noise at either the reference electrodes or the signal electrodes can degrade the measurement of physiological signals or interfere with the selective stimulation or deactivation of specific types of muscle fibers, nerves, or other types of physiological pathways within the body. To reduce the amount of electrical noise that is detected by signal electrodes in an array or the reference, the array and reference can be electrically shielded using an electrically shielded containment system. The containment system is designed to shield the array from various types of electrical noise that can occur both within a body and from sources external to the body.

In one embodiment, the electrode array can include a system for wireless transmission of information. The wireless system can be integrated with the electrode array to allow information to be communicated to the array and detected signals to be transmitted from the array. The electrode array can also include a remote system for charging the array. For example, an inductive power coupling system can be integrated into the array to allow power to be inductively coupled to the array through a surface such as a person's skin. This enables the array to be operably inserted at a desired location within a body. The wireless communication system and power coupling system enables the array to operate for extended periods within the body without the need for external connections. The wireless communication can include two portions, e.g. inductive power link and associated commands to the chip via modulation of that signal, and communications associated with data sent via RF telemetry from the chip to an extrinsic antenna or receiver such as a handheld device or external wireless capable computer.

In order for the wireless communications system and inductive power system to function in cooperation with the electrically shielded containment system, the electrically shielded containment system is specially designed. Additionally, the electrically shielded containment system is configured to provide minimal disruption to the normal physiological operation of the muscle fibers, nerves, or other types of physiological pathways to which the microelectrode array is coupled. Solid surfaces, such as a metal foil, may interrupt the flow of fluids within the body, cause a buildup of hydrostatic pressure, or otherwise interfere with the normal physiological operations. Therefore, the electrically shielded containment system is designed to minimize these types of disruptive conditions.

Figure 3A:
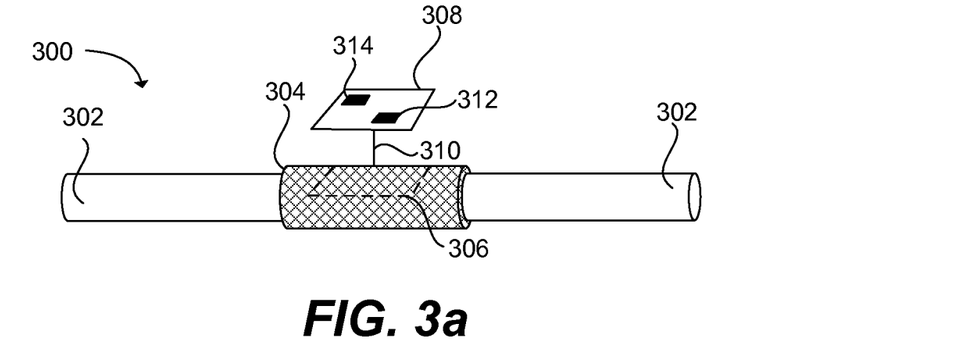
FIG. 3a is a perspective view of an illustration of an electrically shielded containment system used to substantially block electrical noise at a physiological pathway having an embedded microelectrode array in accordance with an embodiment of the present invention.

FIG. 3a illustrates one exemplary embodiment of an electrically shielded containment system 300. The system can include an electrical shielding wrap 304 that is configured to substantially enclose a microelectrode array system 306 implanted in a physiological pathway 302 such as a nerve fiber or muscle fiber. The microelectrode array could consist of a Utah Slanted Electrode array, or, alternatively, other types of microelectrode arrays or even a single signal microelectrode. The electrical shielding wrap can be formed from a substantially electrically conductive biocompatible material. Non-limiting examples can include gold or a bio-compatible alloy of gold or other biocompatible metals or conductive materials. The wrap can include a plurality of holes that enable fluid communication of physiological fluids within a body between the inside and outside of the wrap. In one embodiment, the wrap can be configured from a gold mesh material. The size of the holes in the mesh can be selected to enable normal physiological processes to occur through the mesh and certain desired electromagnetic signals to pass through the mesh while minimizing electrical noise that can pass through the mesh. The mesh may enclose not only the signal electrodes but also the on-array reference electrodes.

Optionally, an external reference electrode wire having a deinsulated tip (off-array) can be used which is oriented within the electrical shielding wrap. The reference wire could, for example, be attached to the wireless chip within the wrap, or, alternatively, connected to an external reference outside the wrap, for example, with wired arrays. The electrical shielding wrap can be connected to a grounding source. The grounding source may be a reference that is defined as having approximately zero potential. Alternatively, the grounding source may be a true earth ground.

Although the illustrated examples utilize a wireless system, wired systems may also be used in connection with the present invention. For example, in place of wireless communications and/or inductive power, either or both of these can be wired connections to provide data communications and power. In these embodiments, the electrical shielding wrap can completely encompass the system with the wires extending out one or both ends of the wrap. An optional external amplifier can also be oriented outside the electrical shielding wrap. As with the wireless embodiments, an external reference wire can be used. Optionally, the external reference wire can be insulated and connected to the external amplifier with a deinsulated end or tip end oriented inside the electrical shielding wrap.

The electrical shielding wrap 304 can also include additional layers. For example, a biocompatible, substantially non-conductive material can be coupled to an interior of the gold mesh material to provide electrical insulation between the electrical shielding wrap and the microelectrode array system to minimize unintended short circuits between the wrap and the microelectrodes, to provide greater protection of the array from mechanical challenges, to help bind the mesh together an hold it in place; to provide a shape that conforms more closely to the nerve and array, among other possible advantages. Further, the additional layers can include multiple electrical shielding wraps (i.e. conductive material). These additional shielding layers can be concentric or offset. The non-conductive material can also be a mesh material. Alternatively, the mesh material may be coated with a substantially non-conductive material to provide electrical insulation. In one aspect, the shielding can be electrically coupled or uncoupled from the electrical ground at will (e.g. via a connector).

In one embodiment, the electrical shielding wrap 304 can be wrapped substantially completely around a section of the physiological pathway 302. The wrap can be used to substantially enclose the microelectrode array system 306 within the wrap, as illustrated in FIG. 3a. One or more wired connections 310 can be fed through the open ends of the mesh wrap or fed through the mesh wrap to provide the means for electrical communication and power transmission with the microelectrode array system through the electrical shielding wrap. The wired connection(s) may allow extracutaneous connections outside the body. Alternatively, a separate power and/or communication system 308 may be located adjacent to the microelectrode array system but outside of the electrical shielding wrap. The power and communication system can include an integrated power coupling system 314 and/or a wireless communication system 312. The power/communication system can be connected to the micro electrode array using shielded wiring such as twisted shielded pair wiring or coaxial cable to minimize noise within the wiring. The power and/or communication system can enable the microelectrode array system to be integrated within the body and shielded from unwanted electrical noise while still being capable of wireless communication and being powered through electrical induction.

Figure 3B:
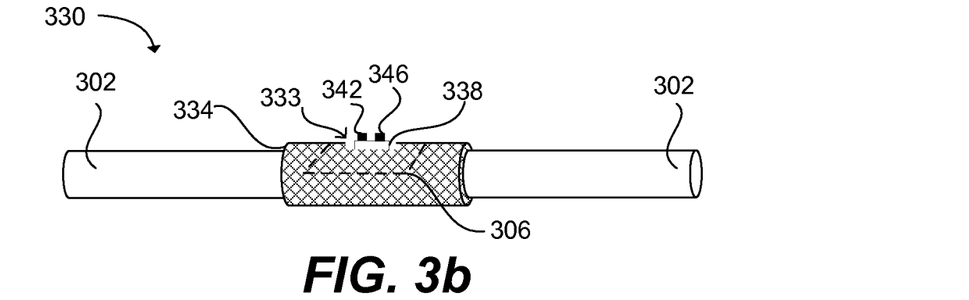
FIG. 3b is a perspective view of an illustration of an electrically shielded containment system with an opening in an electrical shielding wrap in accordance with an embodiment of the present invention.

In another exemplary embodiment, illustrated in FIG. 3b, an electrically shielded containment system 330 is shown. In this embodiment, the electrical shielding wrap 334 can be configured with an opening 333 to allow a communication system 338 integrated with the microelectrode array system 306 that is enclosed within the wrap to communicate while the microelectrode array system is embedded in a physiological pathway 302 such as a nerve fiber or muscle fiber. The opening can be made large enough to allow the circuitry to be located outside the mesh enclosure to enable communication with and powering of the microelectrode array while it is implanted at a subcutaneous location within a body. The communications system can include a wireless communication system 346. Alternatively, the communications system can also include a power supply system 342. In one embodiment, the power supply system can be inductively coupled to a source outside a body to allow the microelectrode array system to be powered. The inductive system can also be used to charge batteries within the microelectrode array system. The electrical shielding wrap can be connected to a grounding source. The grounding source may be a reference that is defined as having approximately zero potential. Alternatively, the grounding source may be a true earth ground.

Figure 3C:
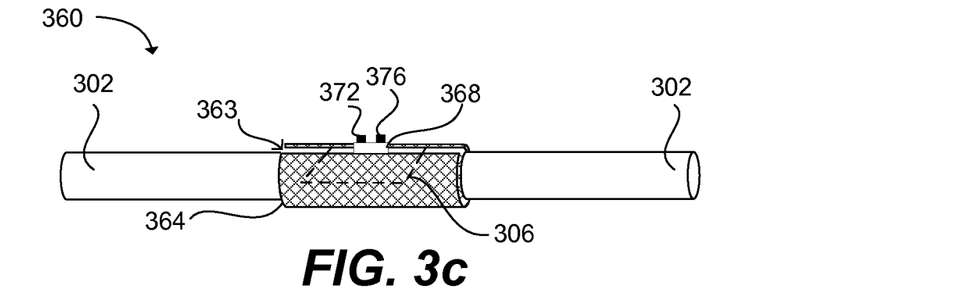
FIG. 3c is a perspective view of an illustration of an electrically shielded containment system with a gap in an electrical shielding wrap in accordance with an embodiment of the present invention.

In another exemplary embodiment, illustrated in FIG. 3c, an electrically shielded containment system 360 is shown. In this embodiment, the electrical shielding wrap 364 can be used to wrap a portion of a section of a physiological pathway 302. Instead of being configured with the type of opening specified above and illustrated in FIG. 3b, the wrap can be left open to form a gap or groove 363 to allow a communication system 368 integrated with the microelectrode array system 306 that is enclosed within the wrap to communicate while the microelectrode array system is coupled to a physiological pathway 302 such as a nerve fiber or muscle fiber. The groove can be made wide enough to allow the necessary circuitry to be located outside the mesh enclosure to enable communication with and powering of the microelectrode array while it is implanted at a subcutaneous location within a body. The communications system can include a wireless communication system 376. In addition, the communications system can also include a power supply system 372. In one embodiment, the power supply system can be inductively coupled to a source outside a body to allow the microelectrode array system to be powered, or batteries within the array system to be charged. The electrical shielding wrap can be connected to a grounding source. The grounding source may be a reference that is defined as having approximately zero potential. Alternatively, the grounding source may be a true earth ground.

Figure 3D:
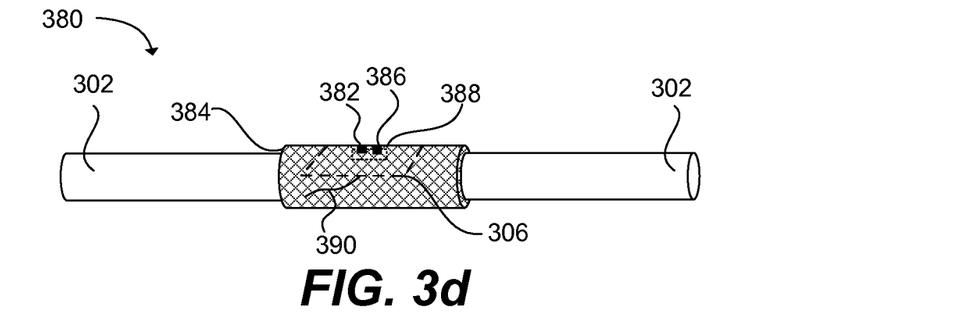
FIG. 3d is a perspective view of an illustration of an electrically shielded containment system fully enclosed within an electrical shielding wrap in accordance with an embodiment of the present invention.

In still another exemplary embodiment, the electrical shielding wrap can be designed to allow the transmission of certain desired electrical and magnetic signals to pass through the shield while blocking other undesired signals. FIG. 3d illustrates an electrically shielded containment system 380 is shown. In this embodiment, the electrical shielding wrap 384 can be used to wrap a section of a physiological pathway 302. In this configuration, the wrap can be completely encompass the pathway. Furthermore, a communication system 388 integrated with the microelectrode array system 306 is also enclosed within the wrap. The communications system can include a wireless communication system 386. Alternatively, the communications system can also include a power supply system 382. As such, the electrical shielding wrap and system can be designed to allow transmission of desired inductive power and communication signals to the system from outside the mesh, e.g. a remote source, and may allow transmission of desired RF telemetry of data while also blocking myoelectric signals/noise (EMG). For example, the signal frequency and amplitude of desired signals can be increased in order to exceed the shielding effect and/or the mesh size or plurality of openings can be adjusted in order to allow desired signals to pass through the wrap. In this manner, a fully integrated wireless array can be completely encompassed within the electrical shielding wrap without compromising the wrap shielding effects or separating components of the system outside the containment system. Optionally, an external reference electrode 390 having a deinsulated tip (off-array) can be used which is oriented within the electrical shielding wrap. In one optional aspect, the electrical shielding wrap can encompass multiple arrays. For example, two or more arrays can be located on a common nerve bundle or an adjacent nerve bundle such that a common electrical shielding wrap can be extended around each array.

In yet another embodiment, one or more electrically conductive meshes or solid foils can be attached to the different muscles or other tissues adjacent to the nerve or other array implant site, rather than being wrapped directly or partially around the nerve or implant site per se. As in other configurations, these meshes could serve as an electrical barrier between the myoelectric events and the neural signals, allowing the latter to be recorded with less contamination by the former. In this way, the enclosing of the array can be an effective enclosing from exposure to undesirable signals which indicates that the wrap is shaped and/or configured more as a wall than a cylindrical enclosure.

The electrical shielding wrap illustrated in the exemplary embodiments of FIGS. 3a, 3b, 3c and 3d can be wrapped around at least a portion of a physiological pathway and attached. For example, the wrap may be attached to the microelectrode array system 306 using a biologically compatible adhesive. For example, a liquid silicon material may be used to bind the electrical shielding wrap around the physiological pathway. Alternatively, if the wrap is fully extended around the pathway, adhesive such as silicon may be applied to the wrap to allow the wrap to be adhesively coupled together. Other means for coupling the wrap such as sewing the wrap closed, using hooks, snaps, Velcro, or other types of fasteners may also be used to attach the wrap around the pathway 302. When the wrap is formed of a porous and/or mesh material, adhesive can more effectively penetrate through the wrap to integrate the wrap with the surrounding pathway. Furthermore, such porous materials can facilitate intergrowth of connective tissue and glial cells through the mesh so as to more fully integrate and secure the wrap around the array system and pathway.

An electrically shielded containment system, such as the exemplary embodiments illustrated in FIGS. 3a, 3b 3c and 3d can be used in conjunction with a microelectrode array 306 with integrated reference electrodes, as previously discussed. By integrating the reference electrodes on the array, the electrically shielded containment system can be used to shield both the signal electrodes and the reference electrodes from electrical noise from sources that are external to the physiological pathway on which the array is connected. The ability to distinguish electrical activity within the pathway from electrical noise external to the pathway can be critical in properly sensing and responding to the electrical activity, as previously discussed with reference to FIGS. 1a and 1b. A reference electrode may also be located outside of the electrode array but within the confines of the electrically shielded containment system.

Summarizing and reiterating to some extent, a microelectrode array system used to sense and stimulate physiological signals has been developed. The microelectrode array includes a array of signal microelectrodes integrated on a dielectric substrate. One or more reference microelectrodes are located adjacent to and integrated with the signal microelectrodes on the dielectric substrate. The reference microelectrodes can be positioned in the array to reduce the level of electrical noise that is detected between the reference microelectrodes and the signal microelectrodes. The microelectrode array can be implanted in a physiological pathway. An electrically shielded containment system can substantially enclose the microelectrode array along a portion of the physiological pathway to substantially block electrical noise at the physiological pathway in a conductive complex physiological solution While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention.

What is claimed is:

1. An electrically shielded containment system used to substantially block electrical noise at a physiological pathway in a conductive complex physiological solution, comprising:
   at least one signal microelectrode configured to penetrate the physiological pathway and being operable for implantation in the physiological pathway;
   at least one reference microelectrode having a lower impedance compared to the at least one signal microelectrode; and
   an electrical shielding wrap configured to substantially enclose the at least one signal microelectrode, the at least one reference microelectrode, and the physiological pathway sufficient to act as a barrier of undesired electrical signals, wherein the electrical shielding wrap is of a porous material and includes a plurality of holes that enable fluid communication of physiological fluids between an inside and outside of the wrap and that enable normal physiological processes to occur.

2. The system of claim 1, wherein the at least one reference microelectrode in an array of microelectrodes is located adjacent to and integrated with the at least one signal microelectrode, to enable the at least one reference microelectrode to be located within the electrical shielding wrap.

3. The system of claim 2, wherein at least one of the reference microelectrodes in the array of microelectrodes is substantially free of insulative material to enable the at least one reference microelectrode to have an impedance of substantially zero ohms.

4. The system of claim 1, wherein the at least one reference microelectrode in an array of microelectrodes is oriented within the electrical shielding wrap but separate from the at least one signal microelectrode as an external reference wire.

5. The system of claim 1, wherein the electrical shielding wrap is coated with an insulative material to reduce short circuiting between the electrical shielding wrap and the at least one signal microelectrode.

6. The system of claim 1, wherein the physiological pathway is selected from the group consisting of a single nerve fiber, a nerve bundle, a muscle fiber, and a muscle fiber bundle.

7. The system of claim 1, wherein the at least one signal microelectrode is completely enclosed within the electrical shielding wrap.

8. The system of claim 1, wherein the at least one signal microelectrode is an array of microelectrodes wherein the signal microelectrodes in the array are substantially perpendicular to and integrated on a dielectric substrate, wherein each signal microelectrode in the array has a predetermined height relative to the dielectric substrate.

9. The system of claim 1, further comprising at least one wire electrically coupled to the at least one signal microelectrode and directed through one of the plurality of holes or through ends of the electrical shielding wrap to enable the at least one signal microelectrode to be connected to at least one of a remote power system and a wireless communication system.

10. The system of claim 1, further comprising at least one of a remote power system and a wireless communication system integrated with the at least one signal microelectrode.

11. The system of claim 10, further comprising an inductive coupling power source configured to provide power to the remote power system integrated with the at least one signal microelectrode.

12. The system of claim 10, wherein the wireless communication system is configured to provide full duplex wireless communication with the at least one signal microelectrode.

13. The system of claim 1, further comprising at least one wire electrically coupled to the at least one signal microelectrode and directed through one of the plurality of holes or through ends of the electrical shielding wrap to enable the at least one signal microelectrode to be connected to at least one of a remote power system and a wired communication system.

14. The system of claim 1, wherein the electrical shielding wrap including the plurality of holes includes a substantially conductive biocompatible mesh material.

15. The system of claim 1, wherein the electrical shielding wrap is oriented between the at least one signal microelectrode and a source of undesirable electrical signals.

16. The system of claim 1, wherein the at least one signal microelectrode is an array of signal microelectrodes wherein the signal microelectrodes in the array are substantially perpendicular to and integrated on a dielectric substrate, wherein each signal microelectrode in the array is individually addressable.

17. The system of claim 1, wherein the at least one signal microelectrode is located in an array of signal microelectrodes wherein the signal microelectrodes in the array are substantially perpendicular to and integrated on a dielectric substrate, wherein each signal microelectrode in the array has a predetermined height relative to the dielectric substrate, wherein the signal microelectrodes are substantially coated with an insulative material to reduce a level of electrical noise received by the signal microelectrodes which have exposed uninsulated tips; and
   wherein the at least one reference microelectrode is located adjacent to and integrated with the signal microelectrodes on the dielectric substrate, wherein the at least one reference microelectrode is positioned on the dielectric substrate relative to the signal microelectrodes to enable a reduced level of electrical noise to be detected between the reference microelectrodes and the signal microelectrodes, wherein each of the at least one reference microelectrode has a greater exposed uninsulated surface area relative to the exposed tips of each of the signal microelectrodes.

18. The system of claim 1, wherein the physiological pathway is a single nerve fiber or a nerve bundle.

19. A method of electrically shielding a physiological pathway to substantially block electrical noise from the physiological pathway in a conductive complex physiological solution, comprising:

implanting at least one signal microelectrode into a patient such that the at least one signal microelectrode is proximate to the physiological pathway;

implanting at least one reference microelectrode having a lower impedance compared to the at least one signal microelectrode; and substantially electrically shielding the at least one signal microelectrode, the at least one reference microelectrode, and a section of the physiological pathway from undesirable electrical signals with an electrical shielding wrap, wherein the electrical shielding wrap is of a porous material and includes a plurality of holes that enable fluid communication of physiological fluids between an inside and an outside of the wrap and that enable normal physiological processes to occur.

20. The method of claim 19, wherein the at least one signal microelectrode is an array of signal microelectrodes oriented on a dielectric substrate.

\* \* \* \* \*